US00PP21869P2

(12) United States Plant Patent
Probst

(10) Patent No.: US PP21,869 P2
(45) Date of Patent: Apr. 12, 2011

(54) ***COREOPSIS* PLANT NAMED 'CALIENTE'**

(50) Latin Name: ***Coreopsis* hybrid**
Varietal Denomination: Caliente

(76) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 12/661,060

(22) Filed: Mar. 10, 2010

(51) Int. Cl.
*A01H 5/00* (2006.01)

(52) U.S. Cl. ..... Plt./417
(58) Field of Classification Search ..... Plt./417
See application file for complete search history.

*Primary Examiner* — Annette H Para
(74) *Attorney, Agent, or Firm* — Penny J. Aguirre

(57) ABSTRACT

A new cultivar of hybrid *Coreopsis* named 'Caliente' characterized by its inflorescences with ray florets that are vibrant red in color with the red blending with orange on the apex of the petals to produce the effect of having an orange-red rim, its bushy and relatively short plant habit, its floriferous and long blooming habit, its relative sterility, and its vigorous growth habit.

2 Drawing Sheets

Botanical classification: *Coreopsis* hybrid.
Variety denomination: 'Caliente'.

CROSS REFERENCE TO A RELATED APPLICATION

This application is co-pending with a U.S. Plant patent application filed for a plant derived from similar parentage in the Inventor's breeding program that is entitled *Coreopsis* Plant Named 'Mambo' (U.S. Plant patent application Ser. No. 12/660,454), *Coreopsis* Plant Named 'Salsa' (U.S. Plant patent application Ser. No. 12/660,464), *Coreopsis* Plant Named 'Limbo' (U.S. Plant patent application Ser. No. 12/660,455), *Coreopsis* Plant Named 'Jive' (U.S. Plant patent application Ser. No. 12/660,491), *Coreopsis* Plant Named 'Cha Cha Cha' (U.S. Plant patent application Ser. No. 12/660,480).

BACKGROUND OF THE INVENTION

The present invention relates to a new and distinct cultivar of *Coreopsis* plant, botanically of hybrid origin and known as *Coreopsis* 'Caliente' and will be referred to hereinafter by its cultivar name, 'Caliente'. The new cultivar of *Coreopsis* is an herbaceous annual grown for use in borders and containers.

The new invention arose from an ongoing controlled breeding program in Hubbardston, Mass. The objective of the breeding program is to develop hybrid cultivars of *Coreopsis* with unique and superior garden attributes. The Inventor crossed *Coreopsis* 'Sweet Dreams' (U.S. Plant Pat. No. 12,720) and *Coreopsis rosea* with *Coreopsis tinctoria* and another annual type species that are not commercialized and made six generations of crosses to produce interspecific hybrids to utilize in his breeding work. The new variety was developed with a goal of producing new cultivars of *Coreopsis* with unique flower colorations, short and bushy plant habits, and sterility to lengthen bloom periods.

The Inventor made a controlled cross in August 2006 in his test garden in Hubbardston, Mass. between two different unnamed F6 generation seedlings produced with crosses of *Coreopsis tinctoria* and *Coreopsis rosea* as the parents. 'Caliente' was selected in August 2007 as a single unique plant amongst the resulting seedlings.

Asexual reproduction of the new cultivar was first accomplished by stem cuttings in Kensington, Conn. in August of 2007 under the direction of the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Caliente' as unique from all *Coreopsis* cultivars known to the Inventor.

1. 'Caliente' exhibits composite inflorescences with ray florets that are vibrant red in color with the red blending with orange on the apex of the petals to produce the effect of having an orange-red rim.
2. 'Caliente' exhibits a bushy plant habit and is relatively short in height; reaching 16 to 24 inches (40 to 61 cm) in height.
3. 'Caliente' exhibits a vigorous growth habit.
4. 'Caliente' exhibits a long blooming period with an abundance of blooms; blooming from June through August in Massachusetts.
5. 'Caliente' is relatively sterile and produces very few seeds if any.

The female parent differs from 'Caliente' in having a shorter plant height (reaching 8 to 12 inches in height), in having inflorescences with ray florets that are white in color with a small burgundy eye, and in producing an abundance of seed that shortens its bloom season to one month. The male parent differs from 'Caliente' in having a taller plant height (reaching up to 30 inches in height), in having a shorter bloom period, and in having inflorescences with ray florets that are red in color but lack the orange-red rim on the petals as observed with 'Caliente'. 'Caliente' can be most closely compared to cultivars from similar parentage, 'Mambo' and 'Salsa'. Both are similar to 'Caliente' in plant habit and blooming habit. 'Mambo' differs from 'Caliente' in having inflorescences with ray florets that are creamy white to rosepurple in color with a burgundy eye zone. 'Salsa' differs from 'Caliente' in having ray florets that are gold in color with a red eye zone.

BRIEF DESCRIPTION OF THE DRAWING

The accompanying colored photographs illustrate the overall appearance and distinct characteristics of the new *Coreopsis*. The photographs in the figures were taken in late summer of a three month-old plants of 'Caliente' as grown outdoors in flats of 4-inch containers in Kensington, Conn.

The photograph in FIG. 1 shows a group of plants of 'Caliente'.

Figure 1:
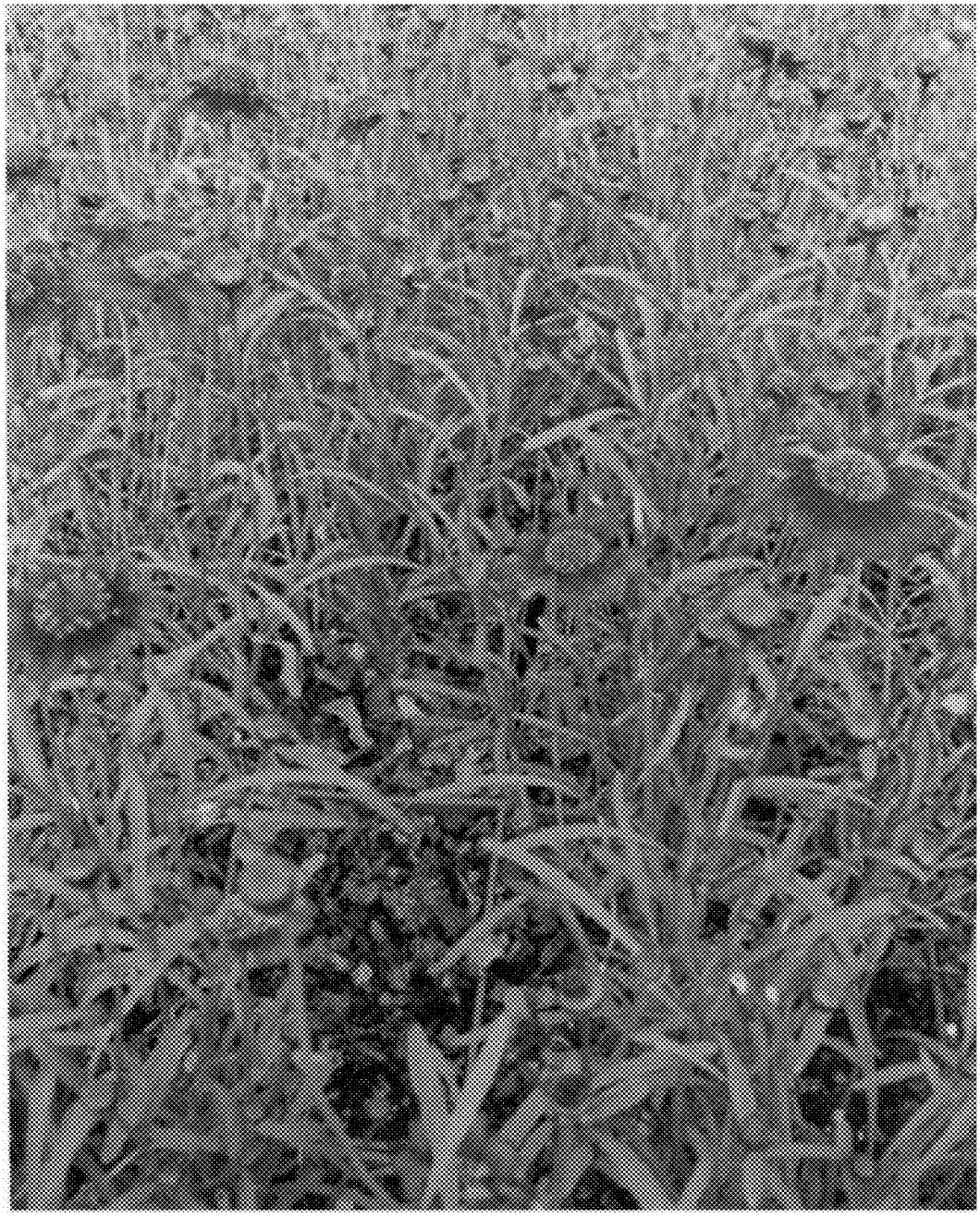
Figure 2:
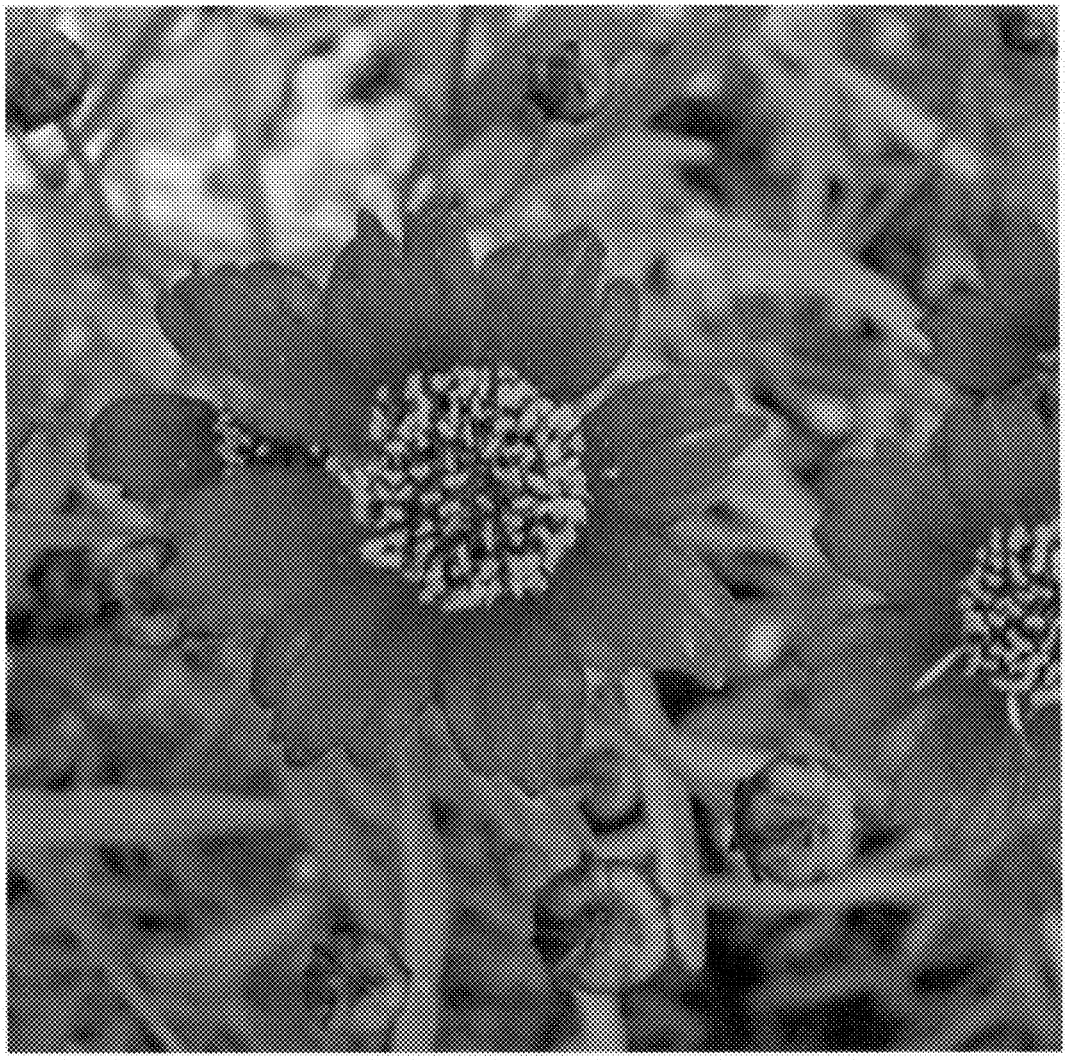

The photograph in FIG. 2 provides a close-up view of an inflorescence of 'Caliente'. The Colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three growing seasons in a trial garden in Hubbardston, Mass. with the detailed botanical data collected from five month-old plants of the new cultivar as grown in two-gallon containers in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from June through August in central Massachusetts.

*Plant habit.*—Herbaceous annual, well-branched to produce a bushy habit.

*Height and spread.*—Reaches 16 to 24 inches (40 to 61 cm) in height and about 24 inches (61 cm) in width in 3 months from a rooted cutting.

*Cold hardiness.*—Has not been tested as it is grown as an annual.

*Diseases resistance.*—No particular resistance or susceptibility has been observed.

*Root description.*—Fibrous, fine and well-branched.

Growth and propagation:

*Propagation.*—Terminal stem cuttings.

*Growth rate.*—Vigorous.

Stem description:

*Shape.*—Oval, solid.

*Stem color.*—144A.

*Stem size.*—Main stem averages 32 cm in length with 4 mm in width, laterals an average of 21 cm in length (excluding peduncles), an average of 3 mm in width and tertiary branches about 15 cm in length and 2 mm in width.

*Stem surface.*—Very finely puberulent with some ridges.

*Branching habit.*—An average of 4 basal branches with an average of 6 lateral branches, and 3 terminal flowering branches on each lateral, branch internode length is variable but typically about 5 cm.

Foliage description:

*Leaf division.*—Simple.

*Leaf margins.*—Tri-lobed, entire or five-lobed.

*Leaf size.*—Up to 10 cm in length and width when five-lobed with side lobes 4 cm in length and 6 mm in width.

*Leaf shape..*—Fan-shaped overall when tri-lobed, ovate in shape when five-lobed, with lobes narrowly lanceolate to linear.

*Leaf base.*—Attenuate.

*Leaf apex.*—Acute.

*Leaf venation.*—Pinnate, not prominent, vein color matches leaf color.

*Leaf attachment.*—Sessile.

*Leaf arrangement.*—Opposite.

*Leaf internode length.*—Variable, an average of 6.5 cm.

*Leaf quantity.*—An average of 10 per lateral stem.

*Leaf surface.*—Dull and very finely puberulent on upper surface and lower surface.

*Leaf color.*—Young and mature upper surface; 137B, young and mature lower surface; 137C.

Flower description:

*Inflorescence type.*—Composite with ray florets surrounding disk florets in the center forming a radiant head, inflorescences are borne singular to group of 3 at terminal of lateral branches.

*Lastingness of inflorescence.*—About one week until senescence of ray flowers, bracts and disk flowers are persistent.

*Fragrance.*—None detected.

*Quantity of inflorescences.*—An average of 20 per lateral branch.

*Inflorescence size.*—Average 1 cm in depth and up to 2.5 cm in diameter with disk portion an average of 8 mm in diameter.

*Inflorescence buds.*—Average of 5 mm in depth and 4 mm in diameter, shape is spherical but flattened, color is a blend of 79B, N34A and 146B, with bracts 146B.

*Peduncle.*—Average of 6 cm in length and 1 mm in diameter, 137B in color, finely puberulent surface.

Involucral bracts:

*Bract number.*—Three rows of 5, one row of outer bracts and two rows of inner bracts.

*Bract arrangement.*—Outer bracts are un-fused spreading and slightly cupped upward, inner bracts overlap and surround receptacle with a campanulate form with apical portion un-fused, spreading, and held close to ray florets.

*Bract size.*—Outer bracts about 2 mm in length and 1.5 mm in width, inner bracts about5 mm in length and 3 mm in width with free portion an average of 3 mm in length and width.

*Bract color.*—Outer bracts 137B in both surfaces, inner bracts; fused portion 137B, un-fused portion is a blend of 23B and 147A.

*Bract texture.*—Outer bract; puberulent, waxy, inner bracts glabrous and waxy.

*Bract apex.*—Outer bract; acute, inner bracts; acute.

*Bract base.*—Truncate.

*Bract shape.*—Outer bracts; ovate, inner bracts; free portion broadly ovate.

Ray florets (sterile):

*Number.*—8.

*Shape.*—Ovate, appearance of three longitudinal sections with center section longer.

*Size.*—Average of 1 cm in length and 7 mm in width.

*Apex.*—Emarginate.

*Base.*—Broadly cuneate.

*Margins.*—Entire on sides, divided into 3 lobes at apex with apex of lobes rounded and center lobe emarginate.

*Aspect.*—Held nearly horizontal and slightly cupped upward.

*Surface.*—Glabrous on both surfaces.

*Color.*—Upper surface opening and fully open; N34A near base becoming blended with N25C and N25D near apex, lower surface opening and fully open; a blend of N34A and N34B.

Disk flowers (male and female):

*Shape.*—Tubular, corolla is fused, flared at apex.

*Size.*—About 5 mm in length and 0.7 mm in width.

*Color.*—En masse; when fully open N77C with tips 14B, corolla; base (tube) is N77B, flared portion is N77C.

*Receptacle.*—About 4 mm in diameter and 1 mm in depth, 144B in color.

Reproductive organs:

*Presence.*—Disk flowers are perfect, ray flowers are sterile.

*Gynoecium.*—1 Pistil, 3.5 mm in length, style is very fine and about 160A in color and translucent, bifid pilose stigma is 7B in color with branches about 1 mm in length and recurved, ovary is 1 mm in length, 0.5 mm in width, inferior, and 145D in color.

*Androcoecium.*—5 stamens, fused into tube surrounding style, 1.5 mm in length and 0.3 mm in width, about 200A in color, pollen is abundant in quantity and 7B in color.

*Fruit/seed.*—Relatively sterile and produces very few seeds if any.

It is claimed:

1. A new and distinct cultivar of *Coreopsis* plant named 'Caliente' as herein illustrated and described.

* * * * *